US008487009B2

(12) United States Patent
Chen et al.

(10) Patent No.: US 8,487,009 B2
(45) Date of Patent: Jul. 16, 2013

(54) 1,2-DIPHENYLETHENE DERIVATIVES FOR TREATMENT OF IMMUNE DISEASES

(75) Inventors: Genhui Chen, Burnaby (CA); John M. Webster, North Vancouver (CA); Jianxiong Li, Port Moody (CA); Wei Liu, Coquitlam (CA)

(73) Assignee: Glaxo Group Limited, Greenford, Middlesex (GB)

( * ) Notice: Subject to any disclaimer, the term of this patent is extended or adjusted under 35 U.S.C. 154(b) by 442 days.

(21) Appl. No.: 12/369,595

(22) Filed: Feb. 11, 2009

(65) Prior Publication Data

US 2009/0149548 A1 Jun. 11, 2009

Related U.S. Application Data

(62) Division of application No. 10/466,879, filed as application No. PCT/CA02/00059 on Jan. 17, 2002, now abandoned.

(60) Provisional application No. 60/322,735, filed on Sep. 18, 2001, provisional application No. 60/262,074, filed on Jan. 18, 2001.

(51) Int. Cl.
*A01N 31/14* (2006.01)
*A61K 31/075* (2006.01)

(52) U.S. Cl.
USPC .......................................... 514/715; 514/717

(58) Field of Classification Search
USPC .......................................... 514/520, 715, 717
See application file for complete search history.

(56) References Cited

U.S. PATENT DOCUMENTS

| | | | | |
|---|---|---|---|---|
| 4,495,191 | A | 1/1985 | Ehrhardt et al. | 514/383 |
| 4,515,883 | A | 5/1985 | Sasaki | 430/58 |
| 4,709,096 | A | 11/1987 | Sasaki | 564/374 |
| 4,920,232 | A | 4/1990 | Goetz et al. | 546/338 |
| 5,210,239 | A | 5/1993 | Abe et al. | 552/307 |
| 5,268,517 | A | 12/1993 | Kober et al. | 570/193 |
| 5,385,942 | A | 1/1995 | Abe et al. | 514/568 |
| 5,434,173 | A | 7/1995 | Chandraratna | |
| 5,478,856 | A | 12/1995 | Suzuki et al. | |
| 5,589,506 | A | 12/1996 | Hashimoto et al. | 514/520 |
| 5,770,620 | A | 6/1998 | Mjalli et al. | 514/415 |
| 5,830,441 | A | 11/1998 | Wang et al. | 424/59 |
| 6,372,749 | B1 | 4/2002 | Okumura et al. | 514/258 |
| 6,413,504 | B1 | 7/2002 | Lakner et al. | 424/60 |
| 6,624,197 | B1 | 9/2003 | Nag et al. | 514/570 |
| 6,689,922 | B1 | 2/2004 | Bernardon | 568/807 |
| 7,371,773 | B2 | 5/2008 | Yamazaki et al. | 514/388 |
| 7,884,228 | B1 | 2/2011 | Laredo | 560/205 |
| 7,902,247 | B2 | 3/2011 | Sinha et al. | 514/396 |
| 7,947,849 | B2 | 5/2011 | Laredo | 560/205 |
| 2004/0259938 | A1 | 12/2004 | Nag et al. | 514/464 |
| 2010/0069486 | A1 | 3/2010 | Morinaga et al. | 514/492 |

FOREIGN PATENT DOCUMENTS

| | | | |
|---|---|---|---|
| CN | 101486666 | A | 7/2009 |
| EP | 0334119 | B1 | 9/1989 |
| EP | 0 245 825 | B1 | 3/1991 |
| FR | 1442295 | A | 6/1966 |
| JP | 05061192 | A | 3/1993 |
| JP | 6009392 | A | 1/1994 |
| JP | 2001261585 | A | 9/2001 |
| WO | 94/20456 | A1 | 3/1994 |
| WO | WO 95/03695 | | 2/1995 |
| WO | 00/26167 | A1 | 5/2000 |
| WO | 01/42231 | A2 | 6/2001 |
| WO | 01/95859 | A2 | 6/2001 |
| WO | WO 02/057219 | A1 | 7/2002 |
| WO | WO 03/024911 | A1 | 3/2003 |
| WO | WO 03/080624 | A2 | 10/2003 |
| WO | WO 2004/031117 | A1 | 4/2004 |

OTHER PUBLICATIONS

Cook et al. ("Colchicine and Related Compounds. Part II. Synthesis of a Simple Analogue of N-Acetylcolchinol Methyl Ether." Journal of the Chemical Society, 1940, 198-200).*
Bogert et al. ("The Preparation and Properties of Certain Methoxylated Carbinols, Olefins and Ketones, Derived from Trimethylgallic Acid" Journal of the American Chemical Society, 1914, 36, 514-530).*
Flynn, Daniel L., et al. "Styrylpyrazoles, styrylisoxazoles, and styrylisothiazoles. Novel 5-lipoxygenase and cyclooxygenase inhibitors", J Med Chem, 34:518-525, 1991.
Hu, Kaiji, et al., "Comparison of metabolities produced in vitro and in vivo by Photorhabdus luminescens, a bacterial symbiont of the entomopathogenic nematode Heterorhabditis megidis", Can J Microbiol, 44:1072-1077, 1998.
Mannila, Erkki, et al., "Anti-leukaemic compounds derived from stilbenes in picea abies bark", Phytochemistry, 33 (4):813-816, 1993.
Ney, U.M., et al. "Anti-inflammatory effects of synthetic effects of synthetic retinoids may be related to their immunomodulatory action", Dermatologica, 175, Suppl. 1, 93-99, 1987.
Thakkar, Kshitij, et al. "Synthesis and protein-tyrosine kinase inhibitory activity of polyhydroxylated stilbene analogues of piceatannol", J Med Chem, 36:2950-2955, 1993.
Treadwell, Edward M., et al., "Synthesis of schweinfurthin C, a geranylated stilbene from Macaranga schweinfurthii", J Org Chem, 64:8718-8723, 1999.
Tudan, Christopher, et al.,"Selective inhibition of protein kinase c, mitogen-activated protein kinase, and neutrophil activation in response to calcium pyrophosphate dihydrate crystals, formyl-methionyl-leucyl-phenylalanine, and phorbol ester by o-(chloroacetyl-carbamoyl) fumagillol (AGM-1470; TNP-470)", Biochemical Pharmacology, 58:1869-1880, 1999.
Waldmann, Thomas A., "The IL-2/IL-2 receptor system: a target for rational immune intervention", Immunology Today, 14(6):264-270, 1993.

(Continued)

*Primary Examiner* — Yong Chong
(74) *Attorney, Agent, or Firm* — Dara L. Dinner; Theodore Furman

(57) ABSTRACT

The invention provides novel 1,2-diphenylethene derivatives and pharmaceutically acceptable salts thereof, the process for production of these compounds and their pharmaceutical composition and the use of these compounds as modulators of T-cells, neutrophils, macrophages and their associated cytokines as agents for treating immune, inflammatory and autoimmune diseases.

21 Claims, No Drawings

OTHER PUBLICATIONS

Marquardt, DL, et al. "Cromolyn inhibition of mediator release in mast cells derived from mouse bone marrow", Am Rev Respir Dis, Jun. 1986, 133(6):1105-9.

Kosaka, Takatoshi, et al., "5-lipoxygenase inhibitors. Synthesis and structure-activity relationship of p-hydroxyaryl-alkenylbenzoazoles", The Pharmaceutical Society of Japan, Sep. 1997, 117(9):611-7.

Agrawal, et al. *Indian Journal of Chemistry*, 68(6): 356-358 (1991).

Binev, et al. *Izvestiya po Khimiya*, 12(2): 228-246 (1979) (CA Abstract).

Caldwell, et al. *Journal of Medicinal Chemistry*, 13(6): 1076-1079 (1970).

Gierer, et al. *Acta Chemica Scandinavica B*., 28: 717-729 (1974).

Jonnalagadda, et al. *Bioorganic & Medicinal Chemistry*, 5(4): 715-722 (1997).

Li, et al. *Yiyao Gongye*, 19(11): 490-492, 501 (1988) (CA Abstract).

Li, et al. *Youji Huaxue*, 10(5): 440-444 (1990).

Muller, et al. *Annalen der Chemie, Justus Liebigs*, 645: 53-65 (1961).

D. Popov. *Nauchni Trudove*, 22: 377-382 (1970) (CA Abstract).

* cited by examiner

1,2-DIPHENYLETHENE DERIVATIVES FOR TREATMENT OF IMMUNE DISEASES

RELATED INFORMATION

This application is a continuation of U.S. Ser. No. 10/466,879, filed Dec. 30, 2003 now abandoned, which is the national stage entry under §371 of PCT/CA02/0059, filed 17 Jan. 2002, which claims the benefit of priority from U.S. Ser. No. 60/262,074, filed 18 Jan. 2001 and U.S. Ser. No. 60/322,735, filed 18 Sep. 2001.

BACKGROUND OF THE INVENTION

Stilbene derivatives have been shown to have a wide range activities and are widely distributed in nature as natural constituentes of plants. There is a growing interest in stilbene derivatives because of a range of activities that have been observed in some of the naturally occurring as well as some of the synthetic stilbenes. Activities include antibiotic (Hu, K., et al., Canadian Journal of Microbiology, 1998, 44, 1072), antileukemic (Mannila, et al., Phytochemistry, 1993, 33, 813), carcinnostatic (EP 641, 767), and protein-tyrosine kinase inhibitory activity (Thakkar, K.; et al., J. Med. Chem., 1993, 36,2950). With the isolation of 5-(2-phenylethenyl)-2-i-propyl-1,3-benzenediol from the bacterial species *Photorhabdus*, a series of its analogues have been designed and synthesized as useful agents or ingredients to treat inflammation and psoriasis and to interfere with protein kinase (Webster et al. WO 01/42231).

It is well established that T lymphocytes (T-cells) play an important role in regulating the immune response. T-cells are closely associated with a wide variety of cytokines such as interleukines (IL), tumor necrosis factors (TNF), interferons (IFN) and granulocyte macrophage colony. T-cell activation and proliferation, and the cytokines associated with them, mediate a wide range of physiological activities in the immune system and in pathogenic inflammation. For example, inhibitors of certain ILs are potentially beneficial for Th2 predominant diseases, while inhibitors of IFN-γ and TNF-α are useful for treatment of Th1 induced immune diseases.

Macrophages are very important components of the host defense system, but they are also involved in the development of tissue injury during inflammation in some human disease. Efficient antagonists can block subsequent symptoms (skin redness, edema, pain and dysfunction) of inflammation. CD86 expression, nitric oxide and TNF-α production are experimental indicators of macrophage function in vivo. CD86 expression by antigen presenting cells including dendritic cells, macrophages and activated B cells is necessary for interaction with T-cell CD28, which is necessary for the T-cells to be fully activated. Nitric oxide is a potent microbiological macrophage product. TNF-α is a pro-inflammatory cytokine important in recruitment and stimulation of inflammatory cells.

Neutrophils predominate over other cell types in many variants of acute and chronic inflammatory conditions. IL-8 is a chemokine produced by neutrophils that in addition to being chemotactic for monocytes and other leukocytes, also activates neutrophils. Down-regulation of neutrophil IL-8 generation may represent a negative feedback mechanism helping to control neutrophil inflammatory activity by preventing further neutrophil recruitment and activation.

Some cytokines mediate a broad inflammatory and immune response as a result of infection or injury and/or other factors. Other cytokines have more specific functions. The complex interplay of these many different cytokine functions with immune cells is essential for the appropriate and optimal immune function. Activation of T-cells is often the initiating event in many of the immune, inflammatory and autoimmune diseases. Accordingly, compounds that can effectively interfere with cytokine formation have utility in preventing and treating related disorders.

IL-2, a 15-kDa protein, is secreted by T-cells upon antigen stimulation and is required for normal immune responsiveness. IL-2 stimulates the proliferation and activation of B and T-cells and is a potent cytokine that can lead to cellular activation and proliferation. IL-2 receptors are found on activated B-Cells, lipolysaccharide treated monocytes, and many T-cells. Clinical studies have shown that interference with IL-2 activity effectively suppresses immune response in vivo [T. A. Waldmann, Immunol. Today, 14, 270 (1993)].

One of the other cytokines is interleukin-8 (IL-8), which has been shown to be a powerful substance for initiating and sustaining inflammatory reactions. IL-8 is also known under the names neutrophil activating peptide or monocyte derived neutrophil activating peptide. It attracts neutrophils by chemotaxis and triggers the release of myeloperoxidase. IL-8 is believed to be associated with diseases such as psoriasis, allergic reactions, rheumatic afflictions and inflammations of the skin and the lungs.

IFN-γ is a member of the interferon family and was produced originally upon mitogenic induction of lymphocytes. IFN-γ is secreted from CD4+ Th1 cells, CD8 cells, gamma/delta T-cells and activated natural killer cells. It plays a role in activating lymphocytes to enhance anti-microbial and anti-tumor effects. In addition, it plays a role in regulating the proliferation, differentiation, and response of lymphocyte subsets. IFN-γ is synthesized by lymphocytes in response to mitogens and induces major histocompatibility complex (MHC) Class II antigen expression. IFN-γ promotes a number of pro-inflammatory aspects of immune responses including the up-regulation of MHC. For a number of autoimmune diseases, the disease-associated inflammatory process is associated with an increased availability of IFN-γ. IFN-γ may have a strong impact on autoimmune disease progression or resolution, actions that may be specific for a particular condition.

Agents that modulate the activities of these cells and the associated cytokine activities are very useful to science and medicine. We now have found many novel stilbene compounds, and have shown that these novel compounds have effect on T lymphocytes, macrophages, neutrophils and mast cells and mediates a variety of immune and inflammatory activities. Accordingly, the invention provides novel compounds, their use, pharmaceutical composition and process for producing these compounds.

SUMMARY OF THE INVENTION

The invention provides novel compounds and pharmaceutically acceptable salts thereof of Formula I

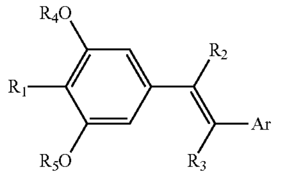

wherein $R^1$ is selected from a). H, b). unsubstituted or substituted alkyl, alkenyl, alkynyl, aryl or aralkyl, c). Halo, d). CN, e). $COOR^6$, f). $NR^7R^8$, g). $S(O)_2NR^7R^8$, h). $COR^9$, i). $OR^{10}$, j). $S(O)_nR^{11}$, n=0-2, and k). substituted or unsubstituted cyclic or heterocyclic groups.

$R^2$ and $R^3$ are independently selected from a group consisting of a). H, b). unsubstituted or substituted alkyl, alkenyl, alkynyl, aryl or aralkyl, c). Halo, d). CN, e). $COOR^6$, f). $NR^7R^8$, g). $S(O)_2NR^7R^8$, h). $COR^9$, i). $OR^{10}$, j). $S(O)_nR^{11}$, n=0-2, and k). substituted or unsubstituted cyclic or heterocyclic groups.

$R^4$ and $R^5$ are independently each selected from the group consisting of a). H, b). unsubstituted or substituted alkyl, cycloalkyl, aryl or aralkyl, and c). Acyl.

$R^6$ is selected from a). H, b). unsubstituted or substituted alkyl, cycloalkyl, aryl or aralkyl.

$R^7$ and $R^8$ are independently selected from a group consisting of a). H, b). unsubstituted or substituted alkyl, cycloalkyl, aryl or aralkyl.

$R^9$ is selected from a). H, b). unsubstituted or substituted alkyl, cycloalkyl, aryl, or aralkyl and c). $NR^7R^8$.

$R^{10}$ is selected from a). H, b). unsubstituted or substituted alkyl, cycloalkyl, aryl, or aralkyl and c). Acyl.

$R^{11}$ is selected from a). H and b). unsubstituted or substituted alkyl, cycloalkyl, aryl or aralkyl.

Ar is selected from a). unsubstituted, mono or multi-substituted phenyl with proviso that $R^2$ and $R^3$ cannot be H simultaneously.

b). unsubstituted, mono or multi-substituted five-member heterocyclic ring containing O, S and/or N and c). unsubstituted, mono or multi-substituted six-member heterocyclic ring containing O, S and/or N.

In a second aspect, this present invention provides the use of the compounds of Formula I as modulators of T-cells, neutrophils, macrophages and their associated cytokines, and particularly as agents for treating inflammatory and autoimmune diseases. This invention also relates to the pharmaceutical composition comprising a compound of the invention and/or salt thereof. In addition, this invention relates to the process for making compounds of Formula I

DETAILED DESCRIPTION OF THE INVENTION

This invention provides compounds of the general Formula I above. Examples of $R^1$ are groups selected from a). H, b). unsubstituted or substituted alkyl, alkenyl, alkynyl, aryl or aralkyl, c). Halo, d). CN, e). $COOR^6$, f). $NR^7R^8$, g). $S(O)_2NR^7R^8$, h). $COR^9$, i). $OR^{10}$, j). $S(O)_nR^{11}$, n=0-2, and k). substituted or unsubstituted cyclic or heterocyclic group. Examples of substitutes for $R^2$ and $R^3$ are independently selected from a group consisting of a). H, b). unsubstituted or substituted alkyl, alkenyl, alkynyl, aryl or aralkyl, c). Halo, d). CN, e). $COOR^6$, f). $NR^7R^8$, g). $S(O)_2NR^7R^8$, h). $COR^9$, i). $OR^{10}$, j). $S(O)_nR^{11}$, n=0-2, and k). substituted or unsubstituted cyclic or heterocyclic group. Examples of substitutes for $R^4$ and $R^5$ are independently each selected from the group consisting of a). H, b). unsubstituted or substituted alkyl, cycloalkyl, aryl or aralkyl, and c). Acyl. Examples of substitutes for $R^6$ is selected from a). H, b). unsubstituted or substituted alkyl, cycloalkyl, aryl or aralkyl. Examples of substitutes for $R^7$ and $R^8$ are independently selected from a group consisting of a). H, b). unsubstituted or substituted alkyl, cycloalkyl, aryl or aralkyl. Examples of substitutes for $R^9$ is selected from a). H, b). unsubstituted or substituted alkyl, cycloalkyl, aryl, or aralkyl and c). $NR^7R^8$. Examples of substitutes for $R^{10}$ is selected from a). H, b). unsubstituted or substituted alkyl, cycloalkyl, aryl, or aralkyl and c). Acyl. Examples of substitutes for $R^{11}$ is selected from a). H and b). unsubstituted or substituted alkyl, cycloalkyl, aryl or aralkyl. Ar is selected from a). unsubstituted, mono or multi-substituted phenyl with proviso that $R^2$ and $R^3$ cannot be H simultaneously. b). unsubstituted, mono or multi-substituted five-member heterocyclic ring containing O, S and/or N and c). unsubstituted, mono or multi-substituted six-member heterocyclic ring containing O, S and/or N. Examples for substituent on Ar are selected independently from a). H, b). unsubstituted or substituted alkyl, alkenyl, alkynyl, aryl or aralkyl, c). Halo, d). CN, e). $COOR^6$, f). $NR^7R^8$, g). $S(O)_2NR^7R^8$, h). $COR^9$, i). $OR^{10}$, j). $S(O)_nR^{11}$, n=0-2 and k). substituted or unsubstituted cyclic or heterocyclic group.

The compounds of the present invention have trans and cis (E and Z) isomers. All stereoisomers of the present compounds, such as those which may exist including trans, cis, forms, are contemplated within the scope of this invention. Individual stereoisomers of the compounds of the invention may, for example, be substantially free of other isomers, or may be admixed.

Preferred compounds are those wherein $R^4$ and $R^5$ are hydrogen, methyl and acetyl. Particularly preferred compounds are those wherein $R^1$ is hydrogen or an alkyl group, $R^4$ and $R^5$ are hydrogen, methyl and acetyl. Highly preferred compounds are the following:

5-(1-Benzyl-2-phenylethenyl)-2-i-propyl-1,3-benzenediol (1).

5-[1-(4-Methylbenzyl)-2-(4-methylphenyl)ethenyl]-2-i-propyl-1,3-benzenediol (2).

5-[1-(3-Fluorobenzyl)-2-(3-fluorophenyl)ethenyl]-2-i-propyl-1,3-benzenediol (3).

5-[1-(3,5-Difluorobenzyl)-2-(3,5-difluorophenyl)ethenyl]-2-i-propyl-1,3-benzenediol (4).

5-(1-Methyl-2-phenylethenyl)-2-i-propyl-1,3-benzenediol (5).

2-(3,5-Dimethoxy-4-i-propylphenyl)-3-phenylpropenylnitrile (6).

2-(3,5-Dihydroxy-4-i-propylphenyl)-3-phenylpropenylnitrile (7).

5-(2,2-Diphenylethenyl)-2-i-propyl-1,3-benzenediol (8).

3-(3,5-Dimethoxy-4-i-propylphenyl)-2-phenylpropenylnitrile (9).

3-(3,5-Dihydroxy-4-i-propylphenyl)-2-phenylpropenylnitrile (10).

1-(3,5-Dimethoxy-4-i-propylphenyl)-2-phenylpropene (11).

5-(2-Methyl-2-phenylethenyl)-2-i-propyl-1,3-benzenediol (12).

1-(3,5-Dimethoxyphenyl)-2-phenylpropene (13).

5-(2-Methyl-2-phenylethenyl)-1,3-benzenediol (14).

2-[2-(3.5-Dimethoxy-4-i-propylphenyl)ethenyl]pyridine (15).

2-[2-(3.5-Dihydroxy-4-i-propylphenyl)ethenyl]pyridine hydrochloride (16).

2-[2-(3.5-Dimethoxy-4-i-propylphenyl)ethenyl]thiophene (17).

2-i-Propyl-5-(2-thiophene-2-ylethenyl)-1,3-benzenediol (18).

2-[2-(3.5-Dimethoxy-4-i-propylphenyl)ethenyl]furan (19).

5-(2-Methyl-2-phenylethenyl)-2-i-propyl-1,3-benzenediol diacetate (20).

2-(3,5-Dihydroxy-4-i-propylphenyl)-3-phenylpropenoic acid (21).

3-(3,5-Dihydroxy-4-i-propylphenyl)-2-phenylpropenoic acid (22).

Compounds of the present invention form salts. Therefore, compounds of the present invention include salts. The term "salts", as used herein, denotes acidic and/or basic salts, formed with inorganic and/or organic acids and bases. Suitable acids include, for example, hydrochloric, sulfuric, nitric, benzenesulfonic, acetic, maleic, tartaric and the like which are pharmaceutically acceptable. It is well known to one skilled in the art that an appropriate salt is chosen based on physical and chemical stability, flowability, hydroscopicity and solubility. While pharmaceutically acceptable salts are preferred, particularly when employing the compounds of the invention as medicaments, other salts find utility, for example, in processing these compounds, or where non-medicament-type uses are contemplated.

In accordance with another aspect of this invention, compounds of this present invention of Formula I are useful as modulators of T-cells, neutrophils, macrophages and their associated cytokines, are of use to conditions mediated by these cells and cytokines. The indications for which the inventive compounds are of use, include in particular, autoimmune and inflammatory conditions and conditions associated with or causal to transplant rejection. Use of the compounds of the present invention includes treatment (including amelioration, reduction, elimination or cure of etiology or symptoms) and/or prevention (including substantial or complete restriction, prophylaxis or avoidance) of disorders associated with the above mentioned activities. Such use is exemplified by, but is not limited to, treating and or preventing a range of disorders such as: transplant [such as organ transplant, acute transplant or heterograft or homograft (such as is employed in burn treatment)] rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenalglands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis, serum sickness; uticaria; allergic diseases such as respiratory allergies (asthma, hay fever, allergic rhinitis) or skin allergies; scleracierma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic sclerosis; morphea and diabetes, restenosis, surgical adhesions, tuberculosis, and chronic inflammatory lung diseases (e.g., asthma, pneumoconiosis, chronic obstructive pulmonary disease, nasal polyps and pulmonary fibrosis).

The present invention also provides use of the inventive compounds for treating and preventing the aforementioned disorders such as atopic. In addition, the compounds of the present invention are useful in degranulation of mast cells and basophils that plays an important role in asthma, allergic rhinitis, and other allergic disease. Compounds of the present invention that block neutrophil activation are useful, for example, in the treatment of ischemia and reperfusion injury.

Compounds of the present invention inhibit induced degranulation and this ability results in additional anti-inflammatory activity for the present compounds beyond their effect on T-cells and neutrophils. In particular, the present compounds are of value for the treatment of asthma, allergic rhinitis, and other instances of allergic disease. The combined activity of the present compounds towards macrophages, neutrophils and T-cells may be of value in the treatment of any of the aforementioned disorders. In a particular embodiment, the compounds of the present invention are useful for the treatment of the aforementioned exemplary disorders irrespective of their etiology, for example, for the treatment of transplant rejection, rheumatoid arthritis, multiple sclerosis, inflammatory bowel disease, lupus, systemic lupus erythematosis, graft vs host disease, T-cell mediated hypersensitivity disease, psoriasis, restenosis, surgical adhesions, tuberculosis, and chronic inflammatory lung diseases (e.g., asthma, pneumoconiosis, chronic obstructive pulmonary disease, nasal polyps and pulmonary fibrosis). Hashimoto's thyroiditis, Guillain-Barre syndrome, cancer, contact dermatitis, allergic disease such as allergic rhinitis, asthma, ischemic or reperfusion injury, or atopic dermatitis.

The present invention provides use of compounds of the present invention in combination with other therapeutic agents. Other therapeutic agents known to those skilled in the art, such as cyclosporin A, FK506 and rapamycin, may be employed with the inventive compounds in the present invention. In the use of the present invention, such other therapeutic agent(s) may be administered prior to, simultaneously with or following the administration of the compound(s) of the present invention.

The present invention also provides pharmaceutical compositions comprising of at least one of the compounds of Formula I capable of treating the aforementioned disorders in an amount effective therefore, and in a pharmaceutically acceptable vehicle or diluent. The compositions of the present invention may contain other agents that are known to those skilled in the art, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The pharmaceutical compositions of the present invention containing the active ingredient may be in a form suitable for systemic, oral and/or topical use. For example, the pharmaceutical compositions may be in the form of a sterile injectable aqueous or oleagenous suspension. This suspension may be formulated according to the known art using those suitable dispersing or wetting agents and suspending agents that have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be formulated in the form of suppositories for rectal administration of the drug. These compositions can be prepared by mixing the drug with a suitable nonirritating excipient that is solid at ordinary temperatures but liquid at the rectal temperature and will therefore melt in the rectum to release the drug. Such materials are cocoa butter and polyethylene glycols.

For oral use as tablets, troches, lozenges, aqueous or oily suspensions, dispersible powders or granules, emulsions, hard or soft capsules, or syrups or elixirs may be formatted. Compositions intended for oral use may be prepared according to any method known to the art for the manufacture of pharmaceutical compositions. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

The pharmaceutical compositions of the invention also may be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soybean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents. Syrups and elixirs may be formulated with sweetening agents, for example glycerol, propylene glycol, sorbitol or sucrose. Such formulations also may contain a demulcent, a preservative and flavoring and coloring agents.

For topical use, creams, ointments, jellies, solutions or suspensions, etc., containing the compound of Formula I is employed. (For purposes of this application, topical application shall include mouth washes and gargles.). Preparation of such topical formulations are well described in the art of pharmaceutical formulations as exemplified by Remington's Pharmaceutical Science, Edition 17, Mack Publishing Company, Easton, Pa. For topical application, these compounds also could be administered as a powder or spray, particularly in aerosol form.

Dosage levels in the order of about 0.01 mg to about 140 mg/kg of body weight per day are useful in the treatment of the above-indicated conditions, or alternatively about 0.5 mg to about 7 g per patient per day. For example, inflammation may be effectively treated by the administration of about 0.01 to 50 mg of the compound per kilogram of body weight per day, or alternatively about 0.5 mg to about 3.5 g per patient per day, preferably 2.5 mg to 1 g per patient per day. It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The amount of active ingredient that may be combined with the carrier materials to produce a single dosage form will vary depending upon the host treated and the particular mode of administration. For example, a formulation intended for oral administration of humans may contain from 0.5 mg to 5 g of active agent compounded with an appropriate and convenient amount of carrier material that may vary from about 5 to about 95 percent of the total composition. Dosage unit forms will generally contain between about 1 mg to about 500 mg of an active ingredient, typically 25 mg, 50 mg, 100 mg, 200 mg, 300 mg, 400 mg, 500 mg, 600 mg, 800 mg, or 1000 mg.

The present invention also provides process of making compounds of the invention. The compounds of this invention may be synthesized by the synthetic methods as described by Webster et al., WO 01/42231, and other related literatures (Treadwell et al. J. Org. Chem. 1999 (64), 8718-8723; Hashimoto et al., WO 1994/020456), which can be generalized easily. Further, alternative methods or modifications may be used. Examples given herein are for illustration purposes only and are not considered as limitations of this invention. In general, the stilbene structures of the compounds of the invention may be synthesized via the following reaction outlined by schemes 1-3: Wittig olefination (Scheme 1), Grignard reaction (Scheme 2) and condensation (Scheme 3).

Scheme 1. Wittig olefination:

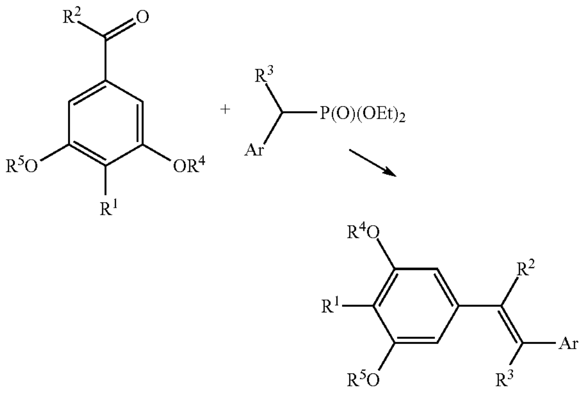

-continued

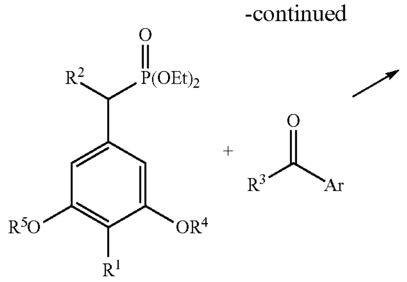

Scheme 2. Grignard reaction:

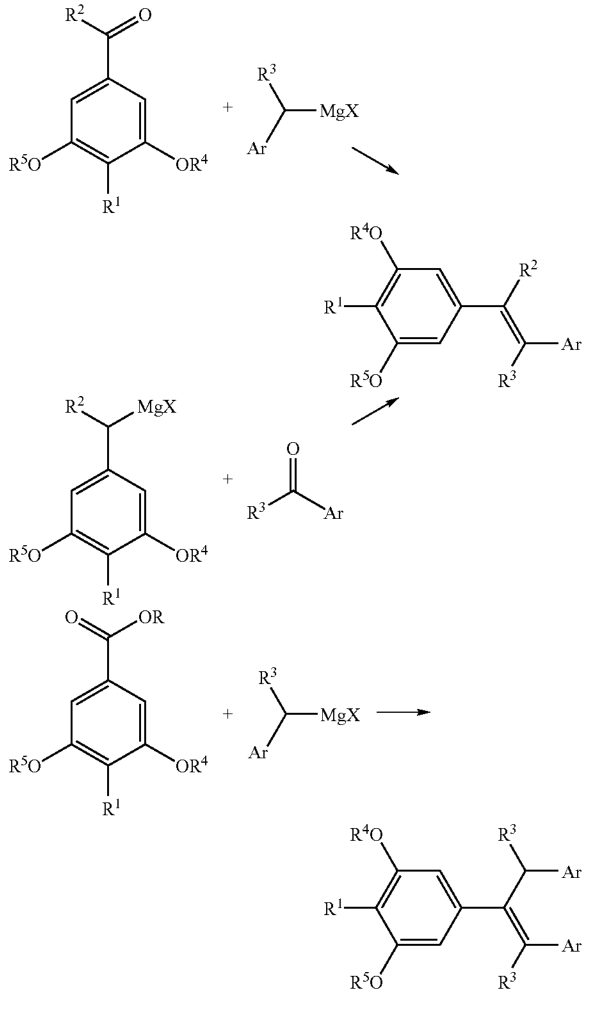

Scheme 3. Aldol condensation:

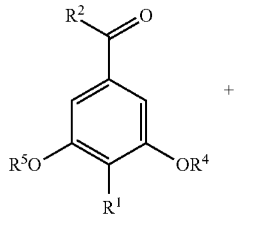

-continued

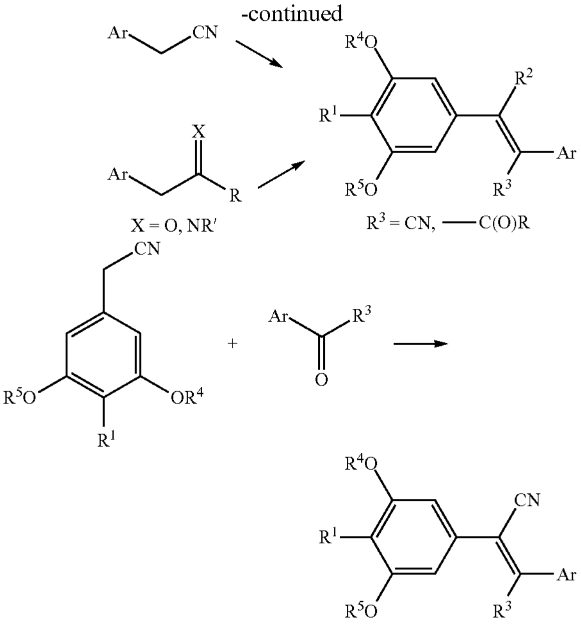

The invention is now described in greater detail by reference to the following non-limiting examples. It will be apparent to those skilled in the art that many modifications, both of materials and methods, may be practiced without departing from the purpose and intent of this disclosure.

EXAMPLE 1

Biological Tests of the Compounds of the Invention

These assays for the following biological activities are well-established and known in the art, only brief descriptions are provided herein for clarity.

1. Effect of the Inventive Compounds on T Lymphocyte (T-Cell) Functions.

T-cell assay is commonly employed as a primary platform for testing of activities that modulate immune and inflammatory activities in many diseases. Assays of antigen non-specific T-cell proliferation and antigen-specific proliferation are often used in the tests.

To determine the effect of the inventive compounds on non-specific and specific antigen induced T-cell proliferation, compounds were tested at a range of concentrations as outlined by the following protocol: Murine lymph nodes were removed aseptically and cell suspensions were prepared in RPMI-1640. Single lymphocytes were isolated over Lymphocyte-M by centrifugation at 22° C. and 1800 g for 15 min, and then washed three times (500 g for 5 min at 22° C.). Adherent cells were depleted by cytoadherence to fibronectin-coated plastic culture dish (twice at 37° C. for 45 min). T-cells isolated by incubating cell suspensions in a nylon wool column for 2 h at 37° C. and use for subsequent experiments were greater than 95% viable, as determined by trypan blue exclusion. Feeder cells were prepared by treating BALB/C spleen cells with mitomycin C (50 μg/ml, for 20 min at 37° C.) followed by five times washing using a large volume of Hank's solution. C57BL/6 Responders ($2\times10^5$) was incubated in duplicate with the mitomycin C treated BALB/C feeder cells ($2\times10^5$) in 96-well, round-bottomed, microtitre plates (Costar Laboratories, Worcester, Mass.) with complete medium (RPMI 1640 with 25 mM Hepes and L-glutamine supplemented with $5\times10^5$M 2-mercapto-ethanol, 10% fetal cow serum (FCS), 10,000 unit of penicillin, and 10 mg of streptomycin per 100 ml of medium) at 37° C., 5% $CO_2$. After 96 h, the culture wells received [$^3$H]thymidine ([$^3$H]TdR; 1 μCi/well) and proliferation was assessed at 16 h by harvesting cells onto glass fiber filter paper and counting in a β-counter.

As shown by the following Table 1, compounds of the present invention had strong activity against T-cell proliferation that is associated with many of disorders mentioned above and these compounds are useful for those disorders.

TABLE 1

Concentration that provides 50% inhibition of T-cell proliferation

| Compound | $IC_{50}$ (μM) |
|---|---|
| 5-(2-Methyl-2-phenylethenyl)-2-i-propyl-1,3-benzenediol | 1.15 |
| 5-(2-Methyl-2-phenylethenyl)-1,3-benzenediol | 4.65 |
| 2-[2-(3.5-Dihydroxy-4-i-propylphenyl)ethenyl]pyridine hydrochloride | 2.09 |
| 2-(3,5-Dihydroxy-4-i-propylphenyl)-3-phenylpropenylnitrile | 3.50 |
| 5-(1-Methyl-2-phenylethenyl)-2-i-propyl-1,3-benzenediol | 1.49 |
| 3-(3,5-Dihydroxy-4-i-propylphenyl)-2-phenylpropenylnitrile | 1.81 |
| 2-i-Propyl-5-(2-thiophene-2-ylethenyl)-1,3-benzenediol | 5.16 |

2. Effect of Inventive Compounds on Cytokine (IL-2, IL-4 And IFN-γ) Production.

To determine the effect of inventive compounds on IL-2, IL-4 and IFN-γ production from activated T-cells, the following assays were performed using the protocol outlined above for T-cells. The T-cell was activated by concanavalin A (Con A) and incubated, cytokines in the supernatants were assayed by commercial immune-linked immunosorbent assay (ELISA) kits.

Data in Table 2 and 3 indicate that compounds of the invention have strong activity on IL-2 and IL-4 production and are useful for treatment of many immune and inflammatory disorders.

TABLE 2

Inhibitory activity against IL-2 production

| Compound | $IC_{50}$ (μM) |
|---|---|
| 5-(2-Methyl-2-phenylethenyl)-2-i-propyl-1,3-benzenediol | 0.40 |
| 5-(2-Methyl-2-phenylethenyl)-1,3-benzenediol | 1.79 |
| 2-(3,5-Dihydroxy-4-i-propylphenyl)-3-phenylpropenylnitrile | 0.13 |
| 2-i-Propyl-5-(2-thiophene-2-ylethenyl)-1,3-benzenediol | 0.028 |

TABLE 3

Inhibitory activity on IL-4 production. Compounds were tested at a concentration of 10 μM and data are expressed as % of control.

| Compounds | % |
|---|---|
| 5-(2-Methyl-2-phenylethenyl)-2-i-propyl-1,3-benzenediol | 0 |
| 5-(2-Methyl-2-phenylethenyl)-1,3-benzenediol | 0 |
| 5-(1-Methyl-2-phenylethenyl)-2-i-propyl-1,3-benzenediol | 01 |
| 5-(2,2-Diphenylethenyl)-2-i-propyl-1,3-benzenediol | 47 |
| 3-(3,5-Dihydroxy-4-i-propylphenyl)-2-phenylpropenylnitrile | 35 |
| 2-i-Propyl-5-(2-thiophene-2-ylethenyl)-1,3-benzenediol | 23 |

Similarly, compounds of the present invention have strong activity on IFN-γ

TABLE 4

Concentration for 50% of inhibition of IFN-γ

| Compounds | $IC_{50}$ (μM) |
|---|---|
| 2-(3,5-Dihydroxy-4-i-propylphenyl)-3-phenylpropenylnitrile | 0.86 |
| 5-(1-Methyl-2-phenylethenyl)-2-i-propyl-1,3-benzenediol | 1.62 |
| 5-(2,2-Diphenylethenyl)-2-i-propyl-1,3-benzenediol | 1.71 |
| 3-(3,5-Dihydroxy-4-i-propylphenyl)-2-phenylpropenylnitrile | 0.71 |
| 2-i-Propyl-5-(2-thiophene-2-ylethenyl)-1,3-benzenediol | 0.08 |

3. Effect on Macrophages and Related Activities.

Macrophages are very important components of the host defense system, but they are also involved in the development of tissue injury during inflammation in some human disease. Efficient antagonists can block subsequent symptoms (skin redness, edema, pain and dysfunction) of inflammation. CD86 expression, nitric oxide and TNF-α production are experimental indicators of macrophage function in vivo. CD86 expression by antigen presenting cells, including dendritic cells, macrophages and activated B cells, is necessary for interaction with T-cell CD28, which is necessary for T-cells to be fully activated. Nitric oxide is a potent microbiological macrophage product. TNF-α is a pro-inflammatory cytokine important in recruitment and stimulation of inflammatory cells. The effect of inventive compounds on the TNF-α production by macrophage cells was tested using the following protocol: Murine macrophage cells were lifted from adherent culture and resuspended in 10% FCS in DMEM. Cells ($5\times10^4$/well) were aliquoted into flat bottom, tissue culture-treated microtitre plates and lipolysaccharide, N-acetylcysteine, test compound or vehicle controls were added. The cells were incubated at 37° C., 5% $CO_2$ for 24 h and the culture supernatant removed for TNF-α ELISA, and CD86 expression was determined by FACS analysis on flow cytometer.

As shown in Table 5 and 6 below, when tested in the above experiment at a concentration of 1 μM compounds of the invention had effect on TNF-α production and CD86 expression.

TABLE 5

Effect of compounds on TNF-α production, compounds were tested at a concentration of 10 μM and data are expressed % of control.

| Compounds | % |
|---|---|
| 5-(2-Methyl-2-phenylethenyl)-1,3-benzenediol | 42 |
| 2-[2-(3.5-Dihydroxy-4-i-propylphenyl)ethenyl]pyridine hydrochloride | 75 |
| 2-(3,5-Dihydroxy-4-i-propylphenyl)-3-phenylpropenylnitrile | 60 |
| 2-i-Propyl-5-(2-thiophene-2-ylethenyl)-1,3-benzenediol | 50 |

TABLE 6

Effect of the inventive compounds on CD86 expression in murine macrophages, compounds were tested at a concentration of 10 μM and data are expressed as % of control.

| Compounds | % |
|---|---|
| 5-(2-Methyl-2-phenylethenyl)-2-i-propyl-1,3-benzenediol | 51 |
| 5-(2-Methyl-2-phenylethenyl)-1,3-benzenediol | 90 |
| 2-[2-(3.5-Dihydroxy-4-i-propylphenyl)ethenyl]pyridine hydrochloride | 88 |
| 5-(1-Methyl-2-phenylethenyl)-2-i-propyl-1,3-benzenediol | 0 |
| 5-(2,2-Diphenylethenyl)-2-i-propyl-1,3-benzenediol | 10 |
| 3-(3,5-Dihydroxy-4-i-propylphenyl)-2-phenylpropenylnitrile | 16 |
| 2-i-Propyl-5-(2-thiophene-2-ylethenyl)-1,3-benzenediol | 2 |

4. Effect on Neutrophils.

Neutrophils predominate over other cell types in many variants of acute and chronic inflammatory condition. Effect of the inventive compounds was tested on human neutrophil activation by chemoattractant [N-formyl-methionyl-luecyl-phenylalanine (FMPL)] and crystal (calcium pyrophosphate dihydrate) using an established protocol (Tudan, C. 1999. Biochem. Pharmacol 58:1869-1880).

Neutrophils were prepared from freshly collected human citrated whole blood. Briefly, 400 ml of blood were mixed with 80 ml of 4% dextran in Hanks buffered saline solution (HBSS) pH 7.4 and allowed to settle for 1 hour. Plasma was collected continuously and 5 ml applied to 5 ml of Ficoll Paque (Pharmacia) in 15 ml polypropylene tubes. Following centrifugation at 500 g for 30 minutes, the neutrophil pellets were washed free of erythrocytes by 20 seconds of hypotonic shock. Neutrophils were resuspended in HBSS, kept on ice and used for experiments within 3 h. Neutrophil viability and purity was always greater than 90%. Solutions of test compounds were added to neutrophils at 5,000,000 cells per ml under mild vortexing. Cells were incubated for 20 minutes at 33° C. then for 10 minutes at 37° C. before addition to crystals or chemoattractants for neutrophil activation. Chemoluminescence was monitored using an luminometer at 37° C.

Results showed that this compound exhibited very strong activity in the test at micromolar concentrations (Table 7). Similarly, this compound has strong inhibitory activity against neutrophil activation induced by chemoattractant, N-formyl-methionyl-luecyl-phenylalanine (Table 8).

TABLE 7

Effect of 5-(2-Methyl-2-phenylethenyl)-2-i-propyl-1,3-benzenediol (25 μM) on crystal induced neutrophil activation, as measured by the chemoluminescence (mV) and data expressed as % of the control.

| Time (minutes) | % |
|---|---|
| 1 | 23 |
| 2 | 10 |
| 3 | 7 |
| 4 | 6 |
| 5 | 6 |
| 7 | 16 |
| 10 | 29 |

TABLE 8

Effect of 25 μM 5-(2-Methyl-2-phenylethenyl)-2-i-propyl-1,3-benzenediol on FMLP induced neutrophil activation, as measured by chemoluminescens.

| | % of control |
|---|---|
| Chemoluminescence (mV) | 30 |

5. Effect on Mediator Release in Mast Cells Derived from Mouse Bone Marrow.

Histamine is an important mediator and is involved in a wide range of biological activities, including inflammation and allergy. The activity of representative compounds, against histamine release was tested using a standard mast cell assay (Arquardt, C. et al. 1986. Am Rev Respir Dis 133:1105-1109). The mast cells were derived from mouse bone marrow. The histamine release was measured by the hexosamindase activity. Table 9. summarizes the activity of 2-i-Propyl-5-(2-thiophene-2-ylethenyl)-1,3-benzenediol.

TABLE 9

Effect of test compounds on histamine release by mast cells.

| Compound | IC50 (μM) |
|---|---|
| 2-i-Propyl-5-(2-thiophene-2-ylethenyl)-1,3-benzenediol | 18.9 |

6. Anti-Inflammatory Activity In Vivo.

The in vivo anti-inflammatory activity was demonstrated using the standard mouse edema animal model. Briefly, Balb/c mouse ear edema was induced by phorbol-12-myristate-13-acetate (TPA) by adding 20 ul of 0.01% (w/v) to the right ear of each mouse. Each test compound dissolved in the same vehicle (ethanol) as TPA was applied separately to the right ear of each moue. The mouse ear edema of each test compound was compared with that of the TPA and expressed as % of inhibition. As summarized in the Table 10 below, 2-(3,5-Dihydroxy-4-i-propylphenyl)-3-phenylpropenylnitrile has very strong anti-inflammatory activity in the animal model.

TABLE 10

In vivo anti-inflammatory efficacy of 2-(3,5-Dihydroxy-4-i-propylphenyl)-3-phenylpropenylnitrile and a commercial anti-inflammatory compound (calcitriol) after a single topical administration in induced edema in Balb/c mouse and data expressed as % of inhibition of edema.

| Treatment compound | % inhibition |
|---|---|
| 2-(3,5-Dihydroxy-4-i-propylphenyl)-3-phenylpropenylnitrile | 85.2 |
| 0.01% calcitriol | 31.2 |

Synthesis of Compounds

Synthetic Example 1

5-(1-Benzyl-2-phenylethenyl)-2-i-propyl-1,3-benzenediol (1)

a). Methyl 3,5-dimethoxy-4-i-propylbenzoate as white crystals was obtained as reported in WO 01/42231 A2 (Chen et al.). $^1$HNMR ($CDCl_3$, ppm): δ 1.32 (d, J=7.2 Hz, 6H), 3.66 (hept, J=7.2 Hz, 1H), 3.82 (s, 6H), 3.95 (s, 3H), 7.25 (s, 2H).

b). 2-(3,5-Dimethoxy-4-i-propylphenyl)-1,3-diphenylpropan-2-ol

To Mg (0.252 g, 10.4 mmol) in dry ether (5 mL) was added benzylbromide (1 mL, 8.41 mL) in dry ether (3 mL) dropwise under reflux. After the addition was complete, the reaction mixture was further refluxed for 1 h. Methyl 3,5-dimethoxy-4-i-propylbenzoate (1.00 g, 4.20 mmol) in ether (15 mL) was added. After the ester completely disappeared, the reaction mixture was cooled to room temperature. Water (10 mL) was added followed by addition of 2N HCl (10 mL) to dissolve precipitate. The organic layer was separated and the aqueous layer was extracted with ether (3×50 mL). The extract was dried over anhydrous $Na_2SO_4$. Evaporation of solvent followed by flash chromatography using ethyl acetate:hexane (1:9) afforded 2-(3,5-dimethoxy-4-i-propylphenyl)-1,3-diphenylpropan-2-ol (1.29 g, 79%) as a white solid. $^1$HNMR ($CDCl_3$, ppm): δ 1.28 (d, J=7.2 Hz, 6H), 3.08 (d, J=13.3 Hz, 2H), 3.35 (d, J=13.3 Hz, 2H), 3.6 (m, 1H), 3.95 (s, 6H), 6.44 (s, 2H), 6.9-7.5 (m, 10H).

c). 5-(1-Benzyl-2-phenylethenyl)-2-i-propyl-1,3-benzenediol (1)

To 2-(3,5-dimethoxy-4-i-propylphenyl)-1,3-diphenylpropan-2-ol (0.63 g, 1.6 mmol) in $CH_2Cl_2$ (10 mL) at −78° C. under $N_2$ was added $BBr_3$ (1M in $CH_2Cl_2$, 5.0 mL, 5.0 mmol) dropwise. After the reaction was stirred at −78° C. for 1 h, the temperature was allowed to rise to room temperature and the reaction mixture was stirred at room temperature over night. Water (50 mL) was added followed by 20% NaOH to adjust pH>12. The organic layer was removed and the aqueous layer was washed with hexane (2×10 mL). The aqueous layer was acidified with 6N HCl to pH 1 and extracted with ether (3×50 mL). The extract was washed with water (10 mL) and brine (10 mL) and dried over anhydrous $Na_2SO_4$. Evaporation of ether followed by flash chromatography using ethyl acetate: hexane (1:9) gave 5-(1-benzyl-2-phenylethenyl)-2-i-propyl-1,3-benzenediol (1).(0.26 g, 47%) as a liquid, which solidified on standing at 0° C. $^1$HNMR ($CDCl_3$, ppm): δ 1.38 (d, J=7.1 Hz, 6H), 3.52 (hept, J=7.1 Hz, 1H), 4.08 (s, 2H), 6.51 (s, 2H), 7.13 (s, 1H), 7.2-7.4 (m, 10H).

Synthetic Example 2

5-[1-(4-Methylbenzyl)-2-(4-methylphenyl)ethenyl]-2-i-propyl-1,3-benzenediol (2)

a). 1,3-Bis(4-methylphenyl)-2-(3,5-dimethoxy-4-i-propylphenyl)propan-2-ol

This material was prepared as a 20% yield from methyl 3,5-dimethoxy-4-i-propylbenzoate and 4-methylbenzyl bromide using the same method as described in example 1 (b). $^1$HNMR ($CDCl_3$, ppm): δ 1.30 (d, J=7.1 Hz, 6H), 2.31 (s, 6H), 3.02 (d, J=13.5 Hz, 2H), 3.25 (d, J=13.5 Hz, 2H), 3.52 (m, 1H), 3.71 (s, 611), 6.45 (s, 2H), 6.8-7.2 (m, 8H).

b). 5-[1-(4-Methylbenzyl)-2-(4-methylphenyl)ethenyl]-2-i-propyl-1,3-benzenediol (2)

A mixture of 2-(3,5-dimethoxy-4-i-propylphenyl)-1,3-bis(4-methylphenyl)propan-2-ol. (0.173 g, 0.41 mmol) obtained above and pyridine hydrochloride (0.432 g, 3.72 mmol) was heated at 200° C. for 3 h under a stream of argon. The reaction mixture was cooled to room temperature. 2NHCl (10 mL) and ether (15 mL) was added. The organic layer was separated and the aqueous was extracted with ether (2×15 mL). The extract was dried over anhydrous $Na_2SO_4$. Evaporation of ether followed by flash chromatography using ethyl acetate: hexane (1:9) gave a pure 5-[1(z)-1-(4-methylbenzyl)-2-(4-methylphenyl)ethenyl]-2-i-propyl-1,3-benzenediol (17.7 mg), a Z/E mixture (79.4 mg) and a pure 5-[1(E)-1-(4-methylbenzyl)-2-(4-methylphenyl)ethenyl]-2-i-propyl-1,3-benzenediol (20.2 mg) in a total yield of 77%. $^1$HNMR ($CDCl_3$, ppm): δ 5-[1(Z)-1-(4-methylbenzyl)-2-(4-methylphenyl)ethenyl]-2-i-propyl-1,3-benzenediol: 1.38 (d, J=7.1 Hz, 6H), 2.28 (s, 3H), 2.36 (s, 3H), 3.5-3.8 (m, 1H), 3.67 (s, 2H), 4.69 (s, 2H), 6.07 (s, 2H), 6.31 (s, 1H), 6.94 (s, 4H), 7.13 (s, 4H). 5-[1(E)-1-(4-methylbenzyl)-2-(4-methylphenyl)ethenyl]-2-i-propyl-1,3-benzenediol: 1.36 (d, J=7.1 Hz, 6H), 2.35 (s, 6H), 3.48 (m, 1H), 4.02 (s, 2H), 4.74 (s, 2H), 6.50 (s, 2H), 7.1-7.3 (m, 9H).

Synthetic Example 3

5-[1-(3-Fluorobenzyl)-2-(3-fluorophenyl)ethenyl]-2-i-propyl-1,3-benzenediol (3)

a). 1,3-Bis(3-fluorophenyl)-2-(3,5-dimethoxy-4-i-propylphenyl)propan-2-ol

This material was prepared in 70% yield from the methyl 3,5-dimethoxy-4-i-propylbenzoate and 3-fluorobenzyl bromide using the same method as described in example 1(b). $^1$HNMR ($CDCl_3$, ppm): δ 1.29 (d, J=7.1 Hz, 6H), 1.85 (s, 1H), 3.07 (d, J=13.3 Hz, 2H), 3.29 (d, J=13.3 Hz, 2H), 3.56 (qint, J=7.1 Hz, 1H), 3.72 (s, 6H), 6.42 (s, 2H), 6.7-7.2 (m, 8H).

b). 5-[1-(3-Fluorolbenzyl)-2-(3-fluorophenyl)ethenyl]-2-i-propyl-1,3-benzenediol (3)

This material was prepared in a total yield of 78% from 1,3-bis(3-fluorophenyl)-2-(3,5-dimethoxy-4-i-propylphenyl)propan-2-ol and pyridine hydrochloride using the same method as described in example 2(b). $^1$HNMR ($CDCl_3$, ppm): δ 5-[1(Z)-1-(3-Fluorolbenzyl)-2-(3-fluorophenyl)ethenyl]-2-i-propyl-1,3-benzenediol: 1.38 (d, J=7.1 Hz, 6H), 3.44 (qint., J=7.1 Hz, 1H), 3.72 (s, 2H), 4.8 (b, 2H), 6.04 (s, 2H), 6.33 (s, 1H), 6.6-7.3 (m, 8H). 5-[1(E)-1-(3-Fluorolbenzyl)-2-(3-fluorophenyl)ethenyl]-2-i-propyl-1,3-benzenediol: 1.38 (d, J=7.1 Hz, 6H), 3.45 (qint., J=7.1 Hz, 1H), 4.03 (s, 2H), 5.00 (s 2H), 6.49 (s, 2H), 6.8-7.3 (m, 9H).

Synthetic Example 4

5-[1-(3,5-Difluorobenzyl)-2-(3,5-difluorophenyl)ethenyl]-2-i-propyl-1,3-benzenediol (4)

a). 1,3-Bis(3,5-difluorobenzyl)-2-(3,5-dimethoxy-4-i-propylphenyl)propan-2-ol

This material was prepared quantitatively from 1,3-difluorobenzyl bromide and methyl 3,5-dimethoxy-4-i-propylbenzoate using the same method as described in example 1(b). $^1$HNMR ($CDCl_3$, ppm): δ 1.28 (d, J=7.0 Hz, 6H), 1.83 (s, 1H), 3.04 (d, J=13.5 Hz, 2H), 3.26 (d, J=13.5 Hz, 2H), 3.56 (qint, J=7.0 Hz, 1H), 3.74 (s, 6H), 6.40 (s, 2H), 6.5-6.8 (m, 6H).

b). 5-[1-(3,5-Difluorobenzyl)-2-(3,5-difluorophenyl)ethenyl]-2-i-propyl-1,3-benzenediol (4)

This material was prepared in a yield of 70% as a Z/E mixture from 1,3-bis(3,5-difluorobenzyl)-2-(3,5-dimethoxy-4-i-propylphenyl)propan-2-ol obtained above and pyridine hydrochloride using the same method as described in example 2 (b). $^1$HNMR ($CDCl_3$, ppm). δ 1.38 (d, J=7.1 Hz, 6H), 3.4 (m, 1H), 3.69, 3.99 (s, 2H), 6.04, 6.47 (s, 2H), 6.28, 6.98 (s, 1H), 6.49-6.78 (m, 6H).

Synthetic Example 5

5-(1-Methyl-2-phenylethenyl)-2-i-propyl-1,3-benzenediol (5)

a). 1-(3,5-Dimethoxy-4-i-propylphenyl)ethanol

To a suspension of Mg (2 g, 82.2 mmol) in dry ether (100 mL) was added $CH_3I$ (5 mL, 80.4 mmol) in dry ether (100 mL). After the addition was completed, the reaction mixture was refluxed for 1 hour and then cooled to 0° C. $LiBH_4$ (2.0M in THF, 25 mL, 50 mmol) was added followed by addition of methyl 3,5-dimethoxy-4-i-propylbenzoate (10.0 g, 42.0 mmol) in dry ether (300 mL). The reaction was stirred at 0° C. overnight. Water (50 mL) was added dropwise followed by 2N HCl (100 mL). The organic layer was separated and the aqueous extracted with ether (4×200 mL). The extract was dried over anhydrous sodium sulfate. Evaporation of the solution yielded a liquid mixture. This was used directly in the next step without purification.

b). Methyl 3,5-dimethoxy-4-i-propylbenzyl ketone

The mixture of the alcohol obtained above and pyridinium chlorochromate (22.64 g, 105.0 mmol) was stirred in $CH_2Cl_2$ (80 mL) for 1 h in the presence of $K_2CO_3$ (2.3 g). The reaction was monitored by TLC. After the reaction was completed (~1 h), the reaction mixture was poured into 600 mL of ether. This was passed through a short florisil pad. The pad was washed thoroughly with ether while the washing was monitored by TLC. Evaporation of solvent followed by flash chromatography using ethyl acetate:hexane (2:98 to 1:9) afforded pure methyl 3,5-dimethoxy-4-i-propylbenzylketone (3.65 g, 39% over two steps) as a white solid. $^1$HNMR ($CDCl_3$, ppm): δ 1.31 (d, J=7.1 Hz, 6H), 2.62 (s, 3H), 3.67 (quint., J=7.1 Hz, 1H), 3.90 (s, 6H), 7.16 (s, 2H).

c). 2-(3,5-Dimethoxy-4-i-propylphenyl)-1-phenyl-propan-2-ol

This compound was prepared from reacting methyl 3,5-dimethoxy-4-i-propylbenzyl ketone obtained above with one equivalent $PhCH_2MgBr$ in 78% yield using the same procedure as described in example 1 (b). $^1$HNMR ($CDCl_3$, ppm): δ 1.32 (d, J=7.1 Hz, 6H), 1.59 (s, 3H), 3.02 (d, J=13.9 Hz, 2H), 3.18 (d, J=13.9 Hz, 2H), 3.61 (quint., J=7.1 Hz, 1H), 3.81 (s, 6H), 6.60 (s, 2H), 7.0-7.4 (m, 6H).

d). 5-(1-Methyl-2-phenylethenyl)-2-i-propyl-1,3-benzenediol (5)

This compound was synthesized from 2-(3,5-dimethoxy-4-i-propylphenyl)-1-phenylpropan-2-ol obtained above and $BBr_3$ in 39% yield by the same procedure as described in example 1(d). $^1$HNMR (DMSO, ppm): δ 1.22 (d, J=7.0 Hz, 6H), 2.12 (s, 3H), 3.4 (m, 1H), 6.44 (s, 2H), 6.69 (s, 1H), 7.3-7.6 (m, 5H), 9.03 (s, 2H).

Synthetic Example 6

2-(3,5-Dimethoxy-4-i-propylphenyl)-3-phenylpropenylnitrile (6)

a). 3,5-Dimethoxy-4-i-propylbenzyl alcohol

To a suspension of $LiAlH_4$ (95%) (5.00 g, 125 mmol) in dry ether (100 mL) at 0° C. was added a solution of methyl 3,5-dimethoxy-4-i-propylbenzoate (17.67 g, 90.1 mmol), obtained in example 1(b) in ether (300 mL) under $N_2$. The suspension was stirred at 0° C. for one hour then for an additional hour at room temperature. The reaction was quenched by slow addition of a saturated $Na_2SO_4$ aqueous solution (10 mL) at 0° C. The mixture was stirred overnight. The solid was filtered off and the filtrate was evaporated to dryness to give 3,5-dimethoxy-4-i-propylbenzyl alcohol (13.76 g, 88.3% yield) as white crystals. $^1$HNMR ($CDCl_3$, ppm): δ 1.34 (d, J=7.2 Hz, 6H), 3.65 (hept., J=7.2 Hz, 1H), 3.88 (s, 6H), 4.70 (s, 2H), 6.62 (s, 2H).

b). 3,5-Dimethoxy-4-i-propylbenzyl bromide

To 3,5-dimethoxy-4-i-propylbenzyl alcohol (12.57 g, 59.8 mmol), obtained above, in dry ether (100 mL) at 0° C. was added $PBr_3$ (3.0 mL, 31.2 mmol) dropwise under nitrogen. The reaction was monitored by TLC. After the reaction was completed (~4 h), water (180 mL) was added. The organic layer was separated and the aqueous layer was extracted with ether (3×50 mL). The extract was washed with water (20 mL), sat. $Na_2CO_3$ (20 mL), water (20 mL) and brine (20 mL), and dried over anhydrous sodium sulfate. Evaporation of the solution yielded the pure bromide. (14.93 g, 91.4%) as a white solid. $^1$HNMR ($CDCl_3$, ppm): δ 1.29 (d, J=7.1 Hz, 6H), 3.64 (hept, J=7.1 Hz, 1H), 3.84 (s, 6H), 4.50 (s, 2H), 6.60 (s, 2H).

c). 3,5-Dimethoxy-4-i-propylbenzylnitrile

A suspension of bromide obtained above (4.81 g, 17.6 mmol) and NaCN (1.64, 33.5 mmol) in DMF (30 mL) was stirred at 50° C. for 2 h. TLC indicated completion of the reaction. The reaction mixture was cooled to room temperature and poured into water (200 mL). White precipitate was collected by filtration. The solid was washed with water (2×50 mL) and dried in air to give 3,5-dimethoxy-4-i-propylbenzylnitrile (3.74 g, 97%). $^1$HNMR ($CDCl_3$, ppm): δ 1.29 (d, J=7.1 Hz, 6H), 3.60 (quint., J=7.1 Hz, 1H), 3.74 (s, 2H), 3.84 (s, 6H), 6.51 (s, 2H).

d). 2-(3,5-Dimethoxy-4-i-propylphenyl)-3-phenyl-propenylnitrile (6)

A mixture of 3,5-dimethoxy-4-i-propylbenzylnitrile (1.00 g, 4.56 mmol), benzylaldehyde (0.49 g, 4.62 mmol) and 20% aq. NaOH (15 drops) was refluxed in ethanol (20 mL) for about 5 h. After the reaction was completed, solution was cooled to room temperature. The acrylonitrile 6 was obtained as yellow, needle-shaped crystals (1.21 g, 86%). $^1$HNMR ($CDCl_3$, ppm): δ 1.32 (d, J=7.1 Hz, 6H), 3.65 (quint., J=7.1 Hz, 1H), 3.91 (s, 6H), 6.85 (s, 2H), 7.4-7.6 (m, 4H), 7.8-8.0 (m, 2H).

Synthetic Example 7

2-(3,5-Dihydroxy-4-i-propylphenyl)-3-phenylpropenylnitrile (7)

This compound was prepared from 6 and $BBr_3$ by the same procedure as described in example 1(c). $^1$HNMR (DMSO, ppm): δ 1.23 (d, J=6.8 Hz, 6H), 3.3-3.4 (m, 1H), 6.27 (s, 1H), 6.63 (s, 2H), 7.38 (s, 1H), 7.5-7.6 (m, 2H), 7.65 (s, 1H), 7.8-7.9 (m, 1H), 9.39 (s, 2H).

Synthetic Example 8

5-(2,2-Diphenylethenyl)-2-i-propyl-1,3-benzenediol (8)

a). 2-(3,5-Dimethoxy-4-i-propylphenyl)-1,1-diphenyl ethanol

This compound was prepared from 3,5-dimethoxy-4-i-propylbenzyl bromide obtained in example 6(b), Mg and benzophenone by the same procedure as described in example 1 (b). $^{1}$HNMR ($CDCl_3$, ppm): δ 1.24 (d, J=7.1 Hz, 6H), 3.3-3.5 (m, 1H), 3.56 (s, 6H), 3.72 (d, J=15.4 Hz, 2H), 6.04 (s, 2H), 7.2-7.7 (m, 10H).

b). 5-(2,2-Diphenylethenyl)-2-i-propyl-1,3-benzenediol (8)

This compound was prepared from 2-(3,5-dimethoxy-4-i-propylphenyl)-1,1-diphenyl ethanol obtained above and $BBr_3$ by the same procedure as described in example 1 (c). $^{1}$HNMR ($CDCl_3$, ppm): δ 1.41 (d, J=7.0 Hz, 6H), 3.39 (m, J=7.0 Hz, 1H), 6.00 (s, 2H), 6.78 (s, 1H), 7.2-7.5 (m, 10H).

Synthetic Example 9

3-(3,5-Dimethoxy-4-i-propylphenyl)-2-phenylpropenylnitrile (9)

a). 3,5-Dimethoxy-4-i-propylbenzyl aldehyde

A mixture of 3,5-dimethoxy-4-i-propylbenzyl alcohol (13.05 g, 62.1 mmol) obtained in example 6(a) and pyridinium chlorochromate (33.92 g, 157 mmol) was stirred in $CH_2Cl_2$ (100 mL) in the presence of $K_2CO_3$ (4.18 g, 30 mmol) for 30 min. Ether (300 mL) was added to quench the reaction. The mixture was passed through a short pad of florisil and the pad was washed thoroughly with ether. Evaporation of the solvent gave 3,5-dimethoxy-4-i-propylbenzyl aldehyde (11.89 g. 92% yield) as a yellowish crystal. $^{1}$HNMR ($CDCl_3$, ppm): δ 1.32 (d, J=7.2 Hz, 6H), 3.68 (hept., J=7.2 Hz, 1H), 3.92 (s, 6H), 7.12 (s, 2H), 9.96 (s, 1H).

b). 3-(3,5-Dimethoxy-4-i-propylphenyl)-2-phenylpropenyinitrile (9)

This compound was prepared from 3,5-dimethoxy-4-i-propylbenzyl aldehyde obtained above and benzylnitrile by the same procedure as described in example 6 (d). $^{1}$HNMR ($CDCl_3$, ppm): 1.33 (d, J=7.1 Hz, 6H), 3.73 (qint., J=7.1 Hz, 1H), 3.91 (s, 6H), 7.15 (s, 2H), 7.4-7.5 (m, 4H), 7.6-7.8 (m, 2H).

Synthetic Example 10

3-(3,5-Dihydroxy-4-i-propylphenyl)-2-phenylpropenylnitrile (10)

This compound was prepared from 3-(3,5-dimethoxy-4-i-propylphenyl)-2-phenylpropenylnitrile (9) and Pyridine hydrochloride by the same procedure as described in example 2 (b). $^{1}$HNMR ($CDCl_3$, ppm): 1.34 (d, J=7.0 Hz, 6H), 3.48 (qint., J=7.0 Hz, 1H), 6.95 (s, 2H), 7.2-7.5 (m, 5H), 7.6-7.7 (m, 1H).

Synthetic Example 11

1-(3,5-Dimethoxy-4-i-propylphenyl)-2-phenylpropene (11)

To a solution of diethyl (1-phenylethyl)phosphonate (8.72 g, 36.0 mmol) in THF (100 mL) at 0° C. was added NaH (60% in mineral oil) (2.95 g, 73.8 mmol) under $N_2$. After the addition was completed, the suspension was stirred at 0° C. for 1 h and 3,5-dimethoxy-4-i-propylbenzyl aldehyde (7.24 gg, 34.8 mmol), obtained in example 9(a), in THF (100 mL) was added. The reaction was kept at 0° C. for 1 h and then at 45-50° C. for 10 h. The reaction was cooled to 0° C. Water (50 mL) was added slowly to quench the reaction followed by addition of 2N HCl (200 mL). The mixture was extracted with ether (3×200 mL). The extract was dried over anhydrous $Na_2SO_4$. Evaporation of ether gave a crude 1-(3,5-dimethoxy-4-i-propylphenyl)-2-phenylpropene. A small portion of the crude product was purified by flash chromatography using 10% ethyl acetate in hexane to afford pure product. $^{1}$HNMR ($CDCl_3$, ppm): δ 1.33 (d, J=7.1 Hz, 6H), 2.37 (d, J=1.3 Hz, 3H), 3.64 (hept., J=7.1 Hz, 1H), 3.86 (s, 6H), 6.59 (s, 2H), 6.82 (m, 1H), 7.30-7.61 (m, 5H).

Synthetic Example 12

5-(2-Methyl-2-phenylethenyl)-2-i-propyl-1,3-benzenediol (12)

This compound was made from 1-(3,5-dimethoxy-4-i-propylphenyl)-2-phenylpropene (11) and $BBr_3$ in 63% yield by the same procedure as described in example 1(c). $^{1}$HNMR ($CDCl_3$, ppm): δ 1.42 (d, J=7.0 Hz, 6H), 2.32 (d, J=1.4 Hz, 3H), 3.49 (hept., J=7.0 Hz, 1H), 4.71 (s, 2H), 6.39 (s, 2H), 6.67 (m, 1H), 7.58-7.33 (m, 5H).

Synthetic Example 13

1-(3,5-Dimethoxyphenyl)-2-phenylpropene (13)

This material was synthesized from 3,5-dimethoxybenzyl aldehyde and diethyl (1-phenylethyl)phosphonate in 73% yield by the same method as described in example 11. $^{1}$HNMR ($CDCl_3$, ppm): δ 2.33 (d, J=1.2 Hz, 3H), 3.85 (s, 6H), 6.43 (t, J=2.2 Hz, 1H), 6.56 (d, J=2.2 Hz, 2H), 6.81 (d, J=1.2 Hz, 1H), 7.3-7.7 (m, 5H).

Synthetic Example 14

5-(2-Methyl-2-phenylethenyl)-1,3-benzenediol (14)

This compound was made from 1-(3,5-dimethoxyphenyl)-2-phenylpropene (13). and $BBr_3$. in 63% yield by the same procedure as described in example 1(c). $^{1}$HNMR ($CD_3C(O)CD_3$, ppm): δ 2.21 (d, J=1.5 Hz, 3H), 6.23 (t, J=2.2 Hz, 1H), 6.36 (d, J=2.2Hz, 2H), 6.68 (m, 1H), 7.2-7.6 (m, 5H).

Synthetic Example 15

2-[2-(3.5-Dimethoxy-4-i-propylphenyl)ethenyl]pyridine (15)

a). Diethyl (3,5-dimethoxy-4-i-propylbenzyl)phosphonate

The mixture of 3,5-dimethoxy-4-i-propylbenzyl bromide (5.01 g, 18.3 mmol) obtained in example 6(b) and triethyl phosphite (4.7 mL, 27.4 mmol) was heated at 110-130° C. in the presence of $Bu_4NI$ (0.05 g) overnight. The excess triethyl phosphite was removed under reduced pressure at 110° C. to give the phosphonate (5.58 g, 92%). $^{1}$HNMR ($CDCl_3$, ppm): δ 1.27 (d, J=7.1 Hz, 6H), 1.29 (t, J=7.0 Hz, 6H), 3.12 (d, J=21.5 Hz, 2H), 3.4-3.7 (m, 1H), 3.80 (s, 6H), 4.06 (dt, J=7.1, 7.1 Hz, 4H), 6.50 (d, J=2.6 Hz, 2H).

b). 2-[2-(3.5-Dimethoxy-4-i-propylphenyl)ethenyl] pyridine (15)

This material was prepared from the phosphonate prepared above and pyridine carboxaldehyde in 41% yield as the same way as described example 11. $^1$HNMR ($CDCl_3$, ppm): δ 1.32 (d, J=7.1 Hz, 6H), 3.65 (qint., J=7.1Hz, 1H), 3.88 (s, 6H), 6.81 (s, 2H), 7.15 (d, J=16 Hz, 1H), 7.1-7.2 (m, 1H), 7.4-7.5 (m, 1H), 7.60 (d, J=16 Hz, 1H), 7.70 (ddd, J=7.9, 7.9, 1.8 Hz, 1H), 8.60-8.66 (m, 1H).

Synthetic Example 16

2-[2-(3.5-Dihydroxy-4-i-propylphenyl)ethenyl]pyridine hydrochloride (16)

This material was prepared from 15 obtained in example 15(b) and $BBr_3$ in 27% yield as the similar way as described in example 1 (d), except that 6NHCl was added to ether extract to precipitate 16 out as a hydrochloride salt. $^1$HNMR (DMSO, ppm): δ 1.22 (d, J=7.0 Hz, 6H), 3.51 (qint., J=7.0 Hz, 1H), 6.59 (s, 2H), 7.13 (d, J=16.4, 1H), 7.6-7.9 (m, 2H), 8.3-8.5 (m, 2H), 8.72 (d, J=6.4 Hz, 1H).

Synthetic Example 17

2-[2-(3.5-Dimethoxy-4-i-propylphenyl)ethenyl] thiophene (17)

This material was prepared from diethyl (3,5-dimethoxy-4-i-propylbenzyl)phosphonate obtained in example 15(a) and thiophene carboxaldehyde in 78% yield as the same way as described in the example 15(b), $^1$HNMR ($CDCl_3$, ppm): δ 1.32 (d, J=7.1 Hz, 6H), 3.70 (qint., J=7.1 Hz, 1H), 3.89 (s, 6H), 6.69 (s, 2H), 6.90 (d, J=16 Hz, 1H), 7.0-7.3 (m, 4H).

Synthetic Example 18

2-i-Propyl-5-(2-thiophene-2-ylethenyl)-1,3-benzenediol (18)

This material was prepared from 2-[2-(3.5-dimethoxy-4-i-propylphenyl)ethenyl]thiophene obtained in example 17 and pyridine hydrochloride in 24% yield as the same way as described in example 2(b). $^1$HNMR ($CDCl_3$, ppm): δ 1.40 (d, J=7.1 Hz), 3.47 (qint., J=7.1 Hz, 1H), 4.8 (b, 2H), 6.48 (s, 2H), 6.74 (d, J=16Hz, 1H), 7.0-7.1 (m, 3H), 7.2-7.3 (m, 1H).

Synthetic Example 19

2-[2-3.5-Dimethoxy-4-i-propylphenyl)ethenyl]furan (19)

This material was prepared from diethyl (3,5-dimethoxy-4-i-propylbenzyl)phosphonate prepared in example 15(a) and 2-furaldehyde in 56% yield by the same procedure as described in example 15(b). $^1$HNMR ($CDCl_3$, ppm): δ 1.32 (d, J=7.1 Hz, 6H), 3.62 (hept, J=7.1 Hz, 1H), 3.89 (s, 6H), 6.4-6.5 (m, 2H), 6.68 (s, 2H), 6.85 (d, J=16.2 Hz, 1H), 7.06 (d, J=16.2 Hz, 1H), 7.45 (b, 1H).

Synthetic Example 20

5-(2-Methyl-2-phenylethenyl)-2-i-propyl-1,3-benzenediol diacetate (20)

To 5-(2-Methyl-2-phenylethenyl)-2-i-propyl-1,3-benzenediol (12) (3.93 mmol) and triethylamine (10.8 mmol) in dichloromethane (100 mL) at 0° C. was added acetyl chloride dropwise. The reaction was monitored by TLC. Water (50 mL) was added after the reaction was complete (~30 min.). The organic layer was separated and washed with 2NHCl (30 mL), $H_2O$ (50 mL), saturated $NaHCO_3$ (50 mL), $H_2O$ (50 mL) and brine (50 mL), and dried over anhydrous sodium sulfate. Evaporation of the solution followed by flash chromatography using 5% ethyl acetate in hexane yielded 5-(2-methyl-2-phenylethenyl)-2-i-propyl-1,3-benzenediol diacetate (20).

Synthetic Example 21

2-(3,5-Dihydroxy-4-i-propylphenyl)-3-phenylpropenoic acid (21)

The compound 2-(3,5-Dihydroxy-4-i-propylphenyl)-3-phenylpropenylnitrile (7) was refluxed in 40% KOH until the starting material (7) disappeared. The reaction mixture was cooled to room temperature, 2N HCl was added to adjust the pH to 1. This was extracted with ether three times. The extracts were dried over $Na_2SO_4$. Evaporation of solvent followed by flash chromatography gave compound (21).

Synthetic Example 22

3-(3,5-Dihydroxy-4-i-propylphenyl)-2-phenylpropenoic acid (22)

The compound 3-(3,5-Dihydroxy-4-i-propylphenyl)-2-phenylpropenylnitrile (10) was refluxed in 40% KOH until the starting material (10) disappeared. The reaction mixture was cooled to room temperature, 2N HCl was added to adjust the pH to 1. This was extracted with ether three times. The extracts were dried over $Na_2SO_4$. Evaporation of solvent followed by flash chromatography gave compound (22).

The invention claimed is:

1. A pharmaceutical composition comprising a compound of formula Ib:

Ib

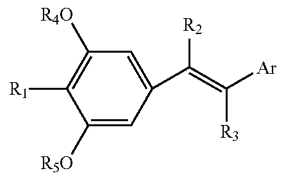

wherein $R^1$ is isopropyl;

$R^2$ is selected from a group consisting of
- a) H,
- b) alkyl, alkenyl, alkynyl, aryl, aralkyl, 4-methylbenzyl, 3-fluorobenzyl, or 3,5-difluorobenzyl,
- c) $COOR^6$,
- d) $NR^7R^8$,
- e) $S(O)_2NR^7R^8$,
- f) $COR^9$,
- g) $OR^{10}$, and
- h) $S(O)_nR^{11}$, n=0–2, $R^3$ is selected from a group consisting of
- a) H,
- b) alkyl, alkenyl, alkynyl, aryl, aralkyl, 4-methylbenzyl, 3-fluorobenzyl, or 3,5-difluorobenzyl,
- c) halo,
- e) $NR^7R^8$,
- f) $S(O)_2NR^7R^8$,
- g) $COR^9$,
- h) $OR^{10}$, and
- i) $S(O)_nR^{11}$, n=0–2, $R^4$ and $R^5$ are independently each selected from the group consisting of
a) H,
b) alkyl, cycloalkyl, aryl or aralkyl, or
c) acyl;
$R^6$ is selected from
a) alkyl, cycloalkyl, aryl or aralkyl
$R^7$ and $R^8$ are independently selected from a group consisting of
a) H, or
b) alkyl, cycloalkyl, aryl or aralkyl;
$R^9$ is selected from
a) H, or
b) alkyl, cycloalkyl, aryl, or aralkyl,
$R^{10}$ is selected from
a) H,
b) alkyl, cycloalkyl, aryl, or aralkyl, or
c) acyl;
$R^{11}$ is selected from
a) H, or
b) alkyl, cycloalkyl, aryl or aralkyl;
Ar is an unsubstituted phenyl, or a phenyl monosubstituted or multisubstituted independently with unsubstituted or substituted alkyl, alkenyl, alkynyl, aryl or aralkyl, halogen, CN, $COOR^6$, $NR^7R^8$, $S(O)_2 NR^7R^8$, $COR^9$, $OR^{10}$, or $S(O)_n R^{11}$ wherein n=0–2;
provided that $R^2$ and $R^3$ cannot be H simultaneously,
the configuration of the double bond is Z or E, or a pharmaceutically acceptable salt thereof; and a pharmaceutically acceptable carrier or excipient.

2. The composition according to claim 1 wherein $R^4$ and $R^5$ are each independently selected from hydrogen, alkyl or acyl.

3. The composition according to claim 2 wherein $R^4$ and $R^5$ are each independently selected hydrogen, methyl or acyl.

4. The composition according to claim 3 wherein $R^4$ and $R^5$ are both hydrogen.

5. The composition according to claim 3 wherein $R^4$ and $R^5$ are both methyl.

6. The composition according to claim 3 wherein $R^4$ and $R^5$ are both acyl.

7. The composition according to claim 1 wherein Ar is an unsubstituted phenyl.

8. The composition according to claim 2 wherein Ar is an unsubstituted phenyl.

9. The composition according to claim 1 wherein Ar is a phenyl mono or multi-substituted with alkyl or halogen.

10. The composition according to claim 9 wherein the alkyl is methyl and the halogen is fluoro.

11. The composition according to claim 10 wherein the Ar is 4-methylphenyl, 3-F-phenyl, or 3,5-difluorophenyl.

12. The composition according to claim 2 wherein Ar is a phenyl mono or multi-substituted with alkyl or halogen.

13. The composition according to claim 12 wherein the Ar is 4-methylphenyl, 3-F-phenyl, or 3,5-difluorophenyl.

14. The composition according to claim 1 wherein $R^2$ and $R^3$ are independently selected from hydrogen, alkyl, $COR^9$, phenyl, benzyl, 4-methylbenzyl, 3-fluorobenzyl, or 3,5-difluorobenzyl.

15. The composition according to claim 2 wherein $R^2$ and $R^3$ are independently selected from hydrogen, methyl, $C(O)CH_3$, phenyl, benzyl, 4-methylbenzyl, 3-fluorobenzyl, or 3,5-difluorobenzyl.

16. The composition according to claim 8 wherein $R^2$ and $R^3$ are independently selected from hydrogen, methyl, $C(O)CH_3$, phenyl, benzyl, 4-methylbenzyl, 3-fluorobenzyl, or 3,5-difluorobenzyl.

17. The composition according to claim 9 wherein $R^2$ and $R^3$ are independently selected from hydrogen, methyl, $C(O)CH_3$, phenyl, benzyl, 4-methylbenzyl, 3-fluorobenzyl, or 3,5-difluorobenzyl.

18. The composition according to claim 1 wherein $R^2$ and $R^3$ are independently selected from hydrogen, alkyl, $COR^9$, phenyl, benzyl, 4-methylbenzyl, 3-fluorobenzyl, or 3,5-difluorobenzyl, $R^4$ and $R^5$ are each independently selected from hydrogen, alkyl or acyl, Ar is an unsubstituted phenyl or Ar is a phenyl mono or multi-substituted with alkyl or halogen.

19. The composition according to claim 1 wherein the compound of Formula Ib is:
5-(1-Benzyl-2-phenylethenyl)-2-i-propyl-1,3-benzenediol;
5-[1-(4-Methylbenzyl)-2-(4-methylphenyl)ethenyl]-2-i-propyl-1,3-benzenediol;
5-[1-(3-Fluorobenzyl)-2-(3-fluorophenyl)ethenyl]-2-i-propyl-1,3-benzenediol;
5-[1-(3,5-Difluorobenzyl)-2-(3,5-difluorophenyl)ethenyl]-2-i-propyl-1,3-benzenediol;
5-(1-Methyl-2-phenylethenyl)-2-i-propyl-1,3-benzenediol;
5-(2,2-Diphenylethenyl)-2-i-propyl-1,3-benzenediol (8);
1-(3,5-Dimethoxy-4-i-propylphenyl)-2-phenylpropene;
5-(2-Methyl-2-phenylethenyl)-2-isopropyl-1,3-benzenediol;
1-(3,5-Dimethoxyphenyl)-2-phenylpropene;
5-(2-Methyl-2-phenylethenyl)-1,3-benzenediol;
5-(2-Methyl-2-phenylethenyl)-2-i-propyl-1,3-benzenediol diacetate;
2-(3,5-Dihydroxy-4-i-propylphenyl)-3-phenylpropenoic acid; or
3-(3,5-Dihydroxy-4-i-propylphenyl)-2-phenylpropenoic acid.

20. The composition according to claim 1 adapted for systemic, oral or topical administration.

21. The composition according to claim 20 adapted for topical administration.

* * * * *